United States Patent
Wei et al.

(10) Patent No.: US 10,342,958 B2
(45) Date of Patent: Jul. 9, 2019

(54) SYSTEM AND METHOD FOR CORRECTING VALVE REGURGITATION

(71) Applicant: Abbott Cardiovascular Systems Inc., Santa Clara, CA (US)

(72) Inventors: Michael F. Wei, Redwood City, CA (US); Anna M. Snell, Belmont, CA (US); Tamer M. Mahmoud, Sunnyvale, CA (US); Scott C. Mosher, San Francisco, CA (US)

(73) Assignee: ABBOTT CARDIOVASCULAR SYSTEMS INC., Santa Clara, CA (US)

( * ) Notice: Subject to any disclaimer, the term of this patent is extended or adjusted under 35 U.S.C. 154(b) by 231 days.

(21) Appl. No.: 15/639,324

(22) Filed: Jun. 30, 2017

(65) Prior Publication Data
US 2019/0001104 A1  Jan. 3, 2019

(51) Int. Cl.
*A61M 25/10* (2013.01)
*A61M 29/02* (2006.01)
(Continued)

(52) U.S. Cl.
CPC ........... *A61M 25/10* (2013.01); *A61F 2/2457* (2013.01); *A61F 2/82* (2013.01); *A61F 2/95* (2013.01);
(Continued)

(58) Field of Classification Search
CPC .. A61B 2017/00243; A61B 2017/0464; A61B 2017/00247; A61B 2017/048; A61B 2018/00392; A61B 2018/00214; A61B 2018/0022; A61B 17/3478; A61B 17/12022; A61B 17/12122;
(Continued)

(56) References Cited

U.S. PATENT DOCUMENTS

| 330,304 A | 11/1885 | Eden |
| 2,045,520 A | 6/1936 | Shepard et al. |

(Continued)

FOREIGN PATENT DOCUMENTS

| DE | 1188793 B | 3/1965 |
| EP | 226966 A2 | 7/1987 |

(Continued)

*Primary Examiner* — David C Eastwood
*Assistant Examiner* — Mohamed G Gabr
(74) *Attorney, Agent, or Firm* — David J. Pitman; Fulwider Patton LLP

(57) ABSTRACT

A method for improving function of a cardiac valve in a patient, the cardiac valve having at least one leaflet that is attached to a papillary muscle: Inserting a balloon, that is in a first uninflated condition and having a first diameter, within tissue that is part of to the papillary muscle, and thereby separating tissue that was previously connected together, by a maximum amount equal to the first diameter; inflating the balloon to a second inflated condition having a second diameter greater than the first diameter, thereby permanently stretching tissue in the papillary muscle and separating the tissue from the first diameter to a maximum amount equal to the second diameter; deflating the balloon to the first uninflated condition, and thereby returning the tissue to a separation of a maximum amount substantially equal to the first diameter; and then removing the balloon from the patient.

20 Claims, 7 Drawing Sheets

(51) Int. Cl.
- *A61F 2/24* (2006.01)
- *A61F 2/95* (2013.01)
- *A61F 2/82* (2013.01)

(52) U.S. Cl.
CPC ....... *A61M 29/02* (2013.01); *A61M 2025/105* (2013.01); *A61M 2025/1093* (2013.01); *A61M 2210/125* (2013.01)

(58) Field of Classification Search
CPC ... A61B 18/1492; A61B 18/24; A61F 2/2457; A61F 2/2451; A61F 2/2454; A61F 2/2466; A61F 2/2487; A61F 2/2439; A61F 2/2481; A61F 2/82; A61F 2/95; A61M 2025/105; A61M 2025/1093; A61M 2210/125; A61M 25/10; A61M 29/02

See application file for complete search history.

(56) References Cited

U.S. PATENT DOCUMENTS

| | | |
|---|---|---|
| 2,139,745 A | 12/1938 | Goodall et al. |
| 2,301,783 A | 11/1942 | Lee et al. |
| 2,748,358 A | 5/1956 | Johnston et al. |
| 3,406,724 A | 10/1968 | Borge et al. |
| 3,467,764 A | 9/1969 | Knapp |
| 3,768,269 A | 10/1973 | Broussard et al. |
| 3,784,239 A | 1/1974 | Neher et al. |
| 3,799,587 A | 3/1974 | Chevalier et al. |
| 3,879,097 A | 4/1975 | Oertle et al. |
| 4,120,521 A | 10/1978 | Parmann et al. |
| 4,140,324 A | 2/1979 | Mulas et al. |
| 4,171,560 A | 10/1979 | Garrett et al. |
| 4,220,381 A | 9/1980 | van der Graaf |
| 4,236,386 A | 12/1980 | Yates et al. |
| 4,278,138 A | 7/1981 | Rowley et al. |
| 4,310,059 A | 1/1982 | Moore |
| 4,329,193 A | 5/1982 | Sznopek et al. |
| 4,385,644 A | 5/1983 | Kaempen |
| 4,399,877 A | 8/1983 | Jackson et al. |
| 4,530,379 A | 7/1985 | Policelli |
| 4,548,428 A | 10/1985 | Ruhle |
| 4,614,369 A | 9/1986 | Overath et al. |
| 4,619,470 A | 10/1986 | Overath et al. |
| 4,630,849 A | 12/1986 | Fukui et al. |
| 4,647,078 A | 3/1987 | Lundy et al. |
| 4,649,960 A | 3/1987 | Policelli |
| 4,679,831 A | 7/1987 | Kielminski et al. |
| 4,701,231 A | 10/1987 | Peters et al. |
| 4,786,536 A | 11/1988 | Kaempen et al. |
| 4,799,544 A | 1/1989 | Curlett |
| 4,810,010 A | 3/1989 | Jones et al. |
| 4,813,715 A | 3/1989 | Policelli |
| 4,865,356 A | 9/1989 | Moore et al. |
| 4,872,519 A | 10/1989 | Kopecki et al. |
| 4,889,318 A | 12/1989 | Sisk et al. |
| 4,893,658 A | 1/1990 | Kimura et al. |
| 4,968,545 A | 11/1990 | Fellman et al. |
| 5,062,914 A | 11/1991 | Fuchs et al. |
| 5,082,314 A | 1/1992 | Aubry et al. |
| 5,097,870 A | 3/1992 | Williams et al. |
| 5,105,854 A | 4/1992 | Cole et al. |
| 5,148,877 A | 9/1992 | MacGregor |
| 5,188,401 A | 2/1993 | Staniforth |
| 5,211,429 A | 5/1993 | Charlson et al. |
| 5,233,737 A | 8/1993 | Policelli |
| 5,236,018 A | 8/1993 | Kobayashi et al. |
| 5,288,109 A | 2/1994 | Auberon et al. |
| 5,332,049 A | 7/1994 | Tew |
| 5,334,801 A | 8/1994 | Mohn |
| 5,398,975 A | 3/1995 | Simmons |
| 5,443,099 A | 8/1995 | Chaussepied et al. |
| 5,507,346 A | 4/1996 | Gano et al. |
| 5,579,854 A | 12/1996 | Barry |
| 5,685,576 A | 11/1997 | Wolfe et al. |
| 5,713,423 A | 2/1998 | Martin et al. |
| 5,816,344 A | 10/1998 | Turner et al. |
| 5,895,079 A | 4/1999 | Carstensen et al. |
| 5,908,049 A | 6/1999 | Williams et al. |
| 5,913,337 A | 6/1999 | Williams et al. |
| 5,921,285 A | 7/1999 | Quigley et al. |
| 5,927,409 A | 7/1999 | Turner et al. |
| 5,944,124 A | 8/1999 | Pomerlau et al. |
| 5,988,695 A | 11/1999 | Corbett et al. |
| 5,989,284 A * | 11/1999 | Laufer ............... A61B 18/24 607/96 |
| 6,113,159 A | 9/2000 | Corbett et al. |
| 6,186,558 B1 | 2/2001 | Komolrochanapom |
| 6,244,631 B1 | 6/2001 | Payne et al. |
| 6,315,002 B1 | 11/2001 | Antal et al. |
| 6,367,564 B1 | 4/2002 | Mills et al. |
| 6,378,633 B1 | 4/2002 | Moore et al. |
| 6,641,434 B2 | 11/2003 | Boyle et al. |
| 6,670,880 B1 | 12/2003 | Hall et al. |
| 6,688,396 B2 | 2/2004 | Floerke et al. |
| 6,734,805 B2 | 5/2004 | Johnson |
| 6,830,467 B2 | 12/2004 | Hall et al. |
| 6,866,306 B2 | 3/2005 | Boyle et al. |
| 6,913,093 B2 | 7/2005 | Hall et al. |
| 7,002,445 B2 | 2/2006 | Hall et al. |
| 7,064,676 B2 | 6/2006 | Hall et al. |
| 7,080,998 B2 | 7/2006 | Hall et al. |
| 7,093,654 B2 | 8/2006 | Hall et al. |
| 7,168,510 B2 | 1/2007 | Boyle et al. |
| 7,201,240 B2 | 4/2007 | Hall et al. |
| 7,277,026 B2 | 10/2007 | Hall et al. |
| 7,299,867 B2 | 11/2007 | Hall et al. |
| 7,413,021 B2 | 8/2008 | Madhavan et al. |
| 7,535,377 B2 | 5/2009 | Hall et al. |
| 2004/0043825 A1 | 3/2004 | Horwood et al. |
| 2007/0102197 A1 | 5/2007 | Rotthaeuser |
| 2008/0012569 A1 | 1/2008 | Hall et al. |
| 2008/0251247 A1 | 10/2008 | Flint et al. |
| 2008/0269876 A1* | 10/2008 | Huynh ............... A61B 17/3468 623/2.11 |
| 2009/0038849 A1 | 2/2009 | Braden et al. |
| 2009/0058675 A1 | 3/2009 | Sugiura |
| 2009/0151926 A1 | 6/2009 | Hall et al. |
| 2010/0175890 A1 | 7/2010 | de Macedo |
| 2011/0042072 A1 | 2/2011 | Villegas et al. |

FOREIGN PATENT DOCUMENTS

| | | |
|---|---|---|
| EP | 264446 A1 | 4/1988 |
| EP | 266810 A2 | 5/1988 |
| EP | 292998 A1 | 11/1988 |
| EP | 361639 A2 | 4/1990 |
| FR | 2656403 A1 | 6/1991 |
| GB | 1522240 A | 8/1978 |
| WO | 9917045 A1 | 4/1999 |

* cited by examiner

SYSTEM AND METHOD FOR CORRECTING VALVE REGURGITATION

BACKGROUND

The present invention relates to systems and methods for correcting deficiencies that may arise in the operation of the human heart, specifically in the operation of valves in the human heart.

An understanding of the human heart, and of deficiencies that may arise in the human heart, may be better understood with reference to the accompanying drawings, FIG. 1 and FIG. 2.

FIG. 1 shows a sectional view of the heart 10 of a human subject. The mitral valve 12 is located between the left atrium 14 and left ventricle 16, generally adjacent to the aortic valve 18. The papillary muscles 20, 22 are finger-like muscular projections that extend from the wall of the left ventricle, as shown. Inelastic tendons, known as the chordae tendineae 24 extend from the antero-lateral papillary muscle 20 and from the postero-medial papillary muscle 22 to the anterior leaflet 26 and posterior leaflet 28 of the mitral valve 12, as shown. In a healthy heart, the point of connection between the antero-lateral papillary muscle 20 is at a level marked as P0 in FIG. 1. When connected at this level in relation to the rest of the heart, the papillary muscle(s) serve, in part, to limit movement of the mitral and tricuspid valve leaflets. During the diastolic phase of the cardiac cycle, the left ventricular myocardium relaxes, thus causing the pressure within the left ventricle to decrease and causing the mitral valve leaflets to open as blood travels from the left atrium into the left ventricle. Thereafter, during the systolic phase of the cardiac cycle, the left ventricle contracts, thereby causing an increase in pressure within the left ventricle. This increase in left ventricular pressure causes the mitral valve leaflets 26, 28 to coapt and close. Concurrently with contraction of the left ventricle, the papillary muscles also contract causing the chordae tendineae to tighten. When the point of connection between the chordae tendineae and the papillary muscle are located at level P0 as shown in FIG. 1, then the tightened chordae tendineae hold the mitral valve leaflets in the proper position for closure of the valve and prevents the mitral valve leaflets from prolapsing through the valve annulus.

Mitral valve regurgitation (also known as mitral insufficiency or mitral incompetence) results when the leaflets of the mitral valve do not fully coapt (i.e., do not close tightly), thus allowing blood to backflow from the left ventricle 16 into the left atrium during the systolic phase of the cardiac cycle. This can result in decreased cardiac output and inadequate perfusion of tissues throughout the body, with various resultant symptoms, including severe fatigue and shortness of breath.

Mitral regurgitation can result from a number of causes. In some cases, mitral regurgitation may result from shortening of one or both of the papillary muscles due to a prior myocardial infarction or cardiomyopathy. Also, in some cases, papillary muscles may shorten due to scar tissue formation in patients who have undergone a type of surgical procedure (i.e., endocardial resection) for the treatment of ventricular arrhythmias. Again, the papillary muscles themselves may be displaced downwardly as a result of ischemic distortion in the wall of the heart, with the result that the cordeae pull down on the leaflets with the same effect as being shortened. When the papillary muscles are shortened or moved, the chorda tendonae may create more traction on the mitral valve leaflets, preventing the leaflets from closing properly during the systolic phase of the cardiac cycle. In some cases, mitral regurgitation may result from the dilation of left ventricular wall to which the papillary muscle is directly attached. In such cases, the left ventricular wall bellows out and causes the papillary muscle/chordae apparatus to be in tension, thereby preventing leaflets from fully coapting. FIG. 2 exemplifies the effect described above where, in the case exemplified, the wall of the heart has moved downward relative to the rest of the heart due to ischemic distortion. Thus, here, the point of connection between the chordae tendineae and the papillary muscle has fallen to the level shown by the mark at P1 in relation to the rest of the heart, from the level at P0 where it was positioned when in full health. As a result, the posterior leaflet 28 has been pulled downwards by about the same amount, thereby preventing the leaflets from coapting during systole.

The prior art has included a number of surgical and interventional procedures aimed at treating mitral regurgitation by lengthening papillary muscle(s) or chordae tendineae. For example, some systems in the prior art describe a system and method for elongating a papillary muscle by attaching a muscle elongating device to the papillary muscle.

Other systems in the prior art describe methods, devices, and systems for the endovascular repair of cardiac valves (particularly the atrioventricular valves and most particularly the mitral valve) wherein interventional tools, catheters and other equipment are advanced though the vasculature and to the heart chambers. The interventional tools and other equipment are then used to modify the valve leaflets, the valve annulus, the chordae tendineae and/or the papillary muscles to improve closure of the mitral valve leaflets.

Further systems describe devices and methods for treatment of mitral regurgitation by deployment of implantable devices within the anterior and posterior interventricular veins, or only in the posterior interventricular vein, to cause medial displacement of the anterior and posterior interventricular veins towards the left ventricular cavity. This in turn causes repositioning of the papillary muscles in a manner that purportedly brings the mitral valve leaflets into proper coaptation during the systolic phase of the cardiac cycle.

Further, United States Patent Application Publication No. 20080269876 describes a system and method for implanting devices and fillers within the papillary muscle itself, with the purpose of "bulking up" the papillary muscle, with the intention of lifting the points of connection of the chordae tendineae. Yet each of these solutions includes disadvantages and further deficiencies. For example the system of implanting a filler within the papillary muscle may itself sometimes result in further lowering the points of connection of the chordae tendineae to papillary muscle, thereby exacerbating the problem and further preventing coaptation of the leaflets.

Thus, there remains a need for the development of new devices and methods for altering the length and/or position of a papillary muscle so as to improve the function of cardiac valves to which the papillary muscle is attached. The present invention addresses these and other needs.

SUMMARY OF THE INVENTION

In one embodiment, the invention is a method for improving function of a cardiac valve in a patient, the cardiac valve having at least one leaflet that is attached to a papillary muscle. The method comprising the steps of inserting an expandable device, that is in a first unexpanded condition and having a first diameter, within tissue that is part of or adjacent to the papillary muscle and thereby, separating tissue that was previously connected together, by a first distance equal to the first diameter. Thereafter, expandable device is expanded to a second expanded condition having a second diameter greater than the first diameter, thereby permanently stretching tissue in the papillary muscle and separating the tissue from the first diameter by a second distance equal to the second diameter. After a period of time, the expandable device is unexpanded to the first unexpanded condition, and thereby the tissue is returned to a separation of a third distance substantially equal to the first diameter. Thereafter, expandable device is removed from the patient. The effect of these steps is designed to allow the tissue of the papillary muscle to extend, and to elevate the chordae tendinae so as to provide better coaptation of valve leaflets. However, it will be apparent to one of ordinary skill that the method does not include leaving any implantable device in the tissue of the muscle.

In some embodiments, inserting an expandable device includes inserting a balloon, and expanding the expandable device includes inflating the balloon. In some embodiments, expanding the expandable device to a second expanded condition includes expanding the expandable device to a second diameter, and leaving the expandable device expanded before unexpanding the expandable device so that a period of time elapses between commencing expansion and commencing unexpansion.

In further embodiments, inserting an expandable device within tissue that is part of or adjacent to the papillary muscle includes inserting the expandable device from outside the heart, through the wall of the heart, and into the tissue.

In yet further embodiments, inserting an expandable device within tissue that is part of or adjacent to the papillary muscle includes inserting the expandable device via an aortic valve and then via a left ventricle before inserting the expandable device within the tissue.

In still further embodiments, the invention includes re-expanding the expandable device after the unexpanding step, and before the removing step. Under such embodiments, re-expanding the expandable device may include taking measurements of the degree of coaptation being achieved by leaflets in the heart before the re-expanding step.

In some embodiments, the invention includes treating a surface of tissue that was previously connected to adjacent tissue with a scar inhibiting agent. Under such embodiments, treating a surface with a scar inhibiting agent may include treating the surface with Neosporin, and in other embodiments it may include applying a cold fluid via micropores in the balloon.

In another aspect, the invention is a method for improving function of a cardiac valve in a heart of a patient, the cardiac valve having at least one leaflet that is attached to a papillary muscle. The method comprising the steps of inserting an expandable device within tissue that is part of or adjacent to the papillary muscle. The expandable device is expanded, and thereby the tissue in the papillary muscle is permanently stretched. The expandable device is then unexpanded; and the expandable device is removed from the patient without leaving any implant device or substance in the papillary muscle.

In some embodiments, expanding the expandable device includes inflating a balloon. In further embodiments, after the expanding step, the device is left expanded for a period of time before the unexpanding step. In further embodiments, inserting an expandable device within tissue that is part of or adjacent to the papillary muscle includes inserting the expandable device from outside the heart, through a wall of the heart, and into the tissue. In yet further embodiments, inserting an expandable device within tissue that is part of or adjacent to the papillary muscle includes inserting the expandable device via an aortic valve and then via a left ventricle before inserting the expandable device within the tissue. In yet further embodiments, the method may further include re-expanding the expandable device after the unexpanding step, and before the removing step. Under this embodiment, re-expanding the expandable device may include taking measurements of a degree of coaptation being achieved by leaflets in the heart before the re-expanding step. Other embodiments may further including treating a surface of tissue that was previously connected to adjacent tissue with a scar inhibiting agent. In some embodiments, treating a surface with a scar inhibiting agent includes treating the surface with Neosporin.

Accordingly, these and other advantages of the invention may be better understood when read in conjunction with the figures, and the detailed description of further embodiments.

DETAILED DESCRIPTION OF THE SOME EMBODIMENTS

The following detailed description, read with the accompanying drawings, are intended to describe some, but not necessarily all, examples or embodiments of the invention. The contents of this detailed description and accompanying drawings do not limit the scope of the invention in any way.

Figure 3:
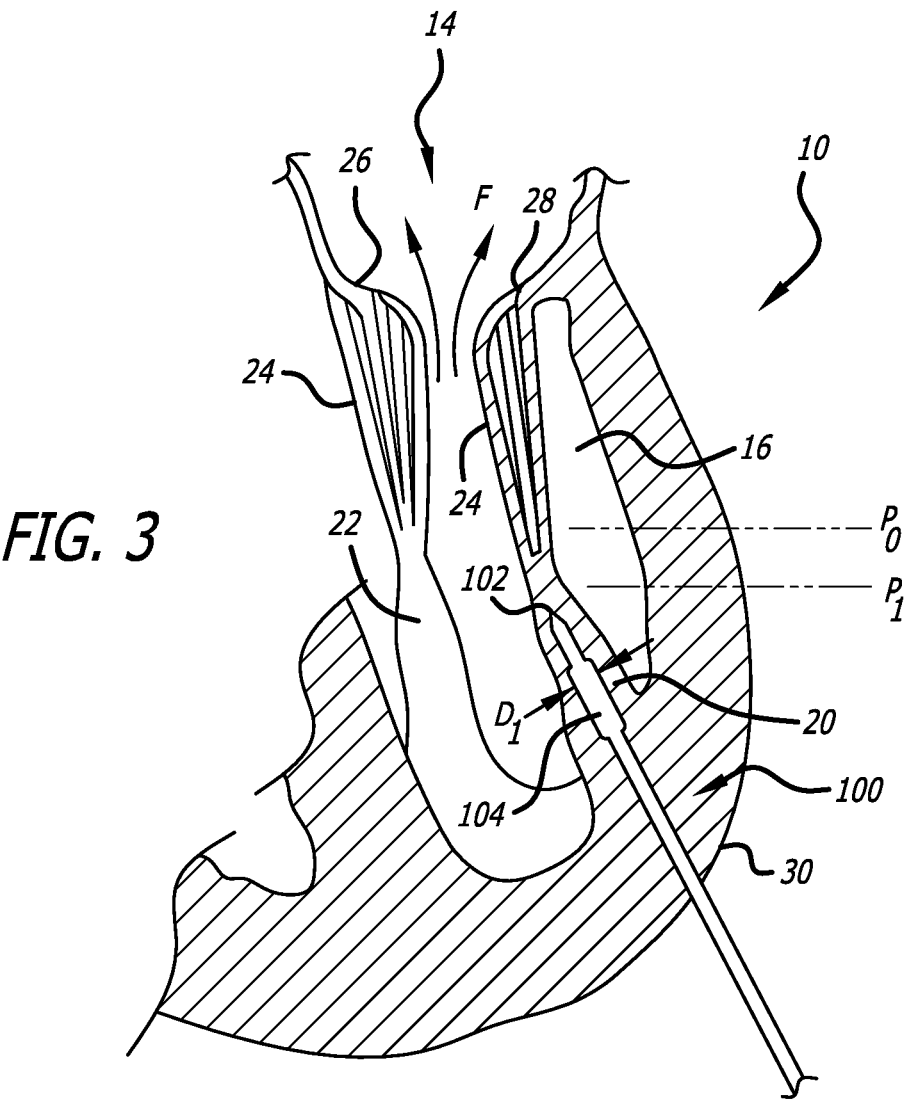
FIG. 3 shows a portion of the heart shown in FIG. 2, into which a balloon cannula has been inserted, with the balloon in an uninflated state.
Figure 4:
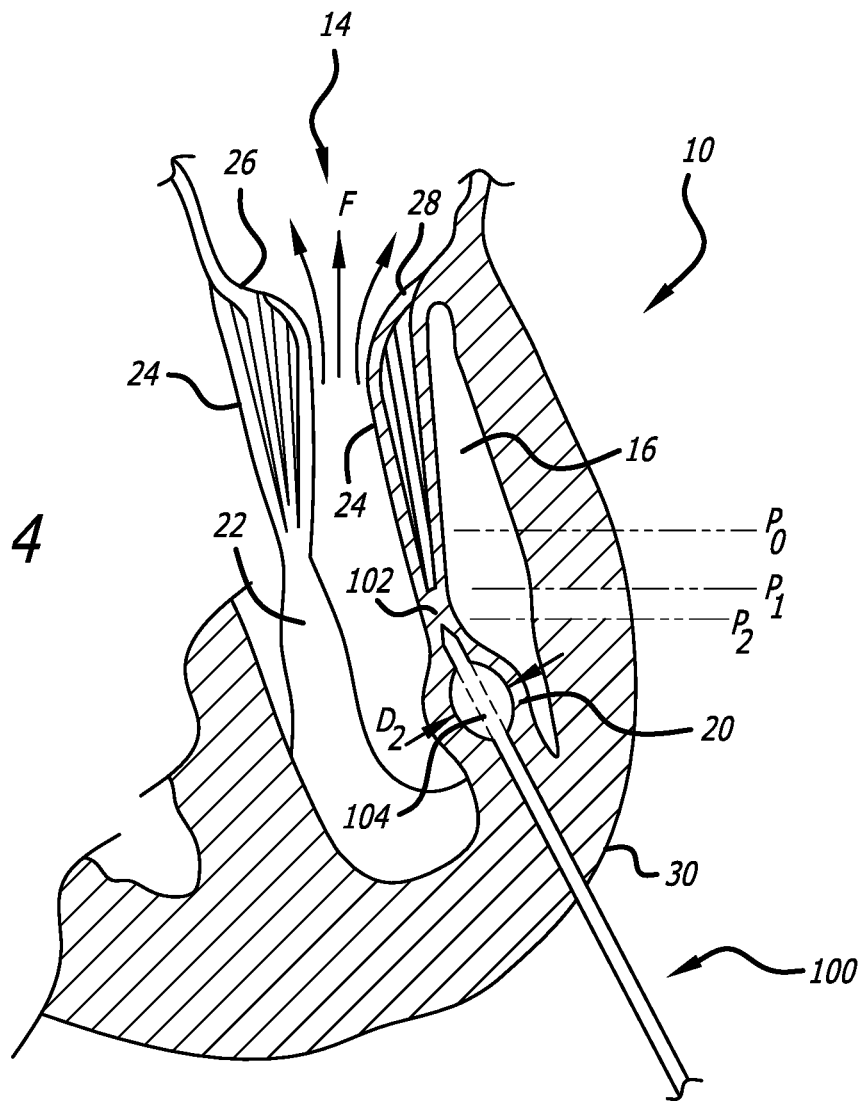
FIG. 4 shows the heart shown in FIG. 3, with the balloon on the cannula in an inflated state.
Figure 5:
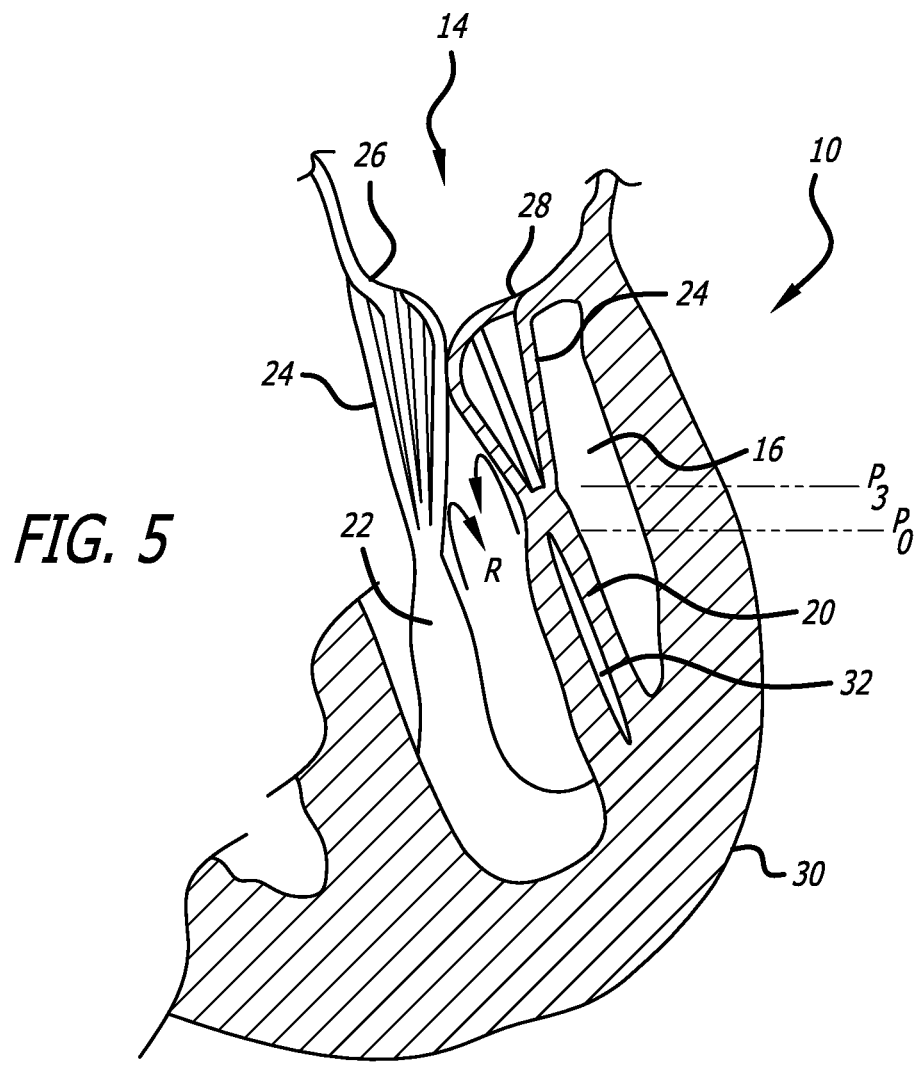
FIG. 5 shows the heart shown in FIG. 2, with the balloon cannula removed from the heart.

With reference to FIGS. 3-5, one embodiment of the invention is described. The embodiment may be carried out as a method by using a tissue penetrating catheter 100 of a kind that is known in the art, schematically shown in FIGS. 3-5, and which is configured to include the following features. The catheter 100 has a distal end capped by a sharp tip 102. Proximal of the tip 102 an inflatable balloon 104 is positioned on the exterior of the catheter, and is fed by inflation medium via a lumen internal to the catheter. The balloon is configured to be expandable when it is positioned inside animal tissue, and to separate layers of tissue from each other and in so doing to stretch the tissue. Catheters generally having these features are known in the art for use in procedures different from the novel procedure described herein. For example U.S. Pat. No. 8,282,665 and the patents recited therein which are incorporated herein by reference, are in this known field.

Figure 1:
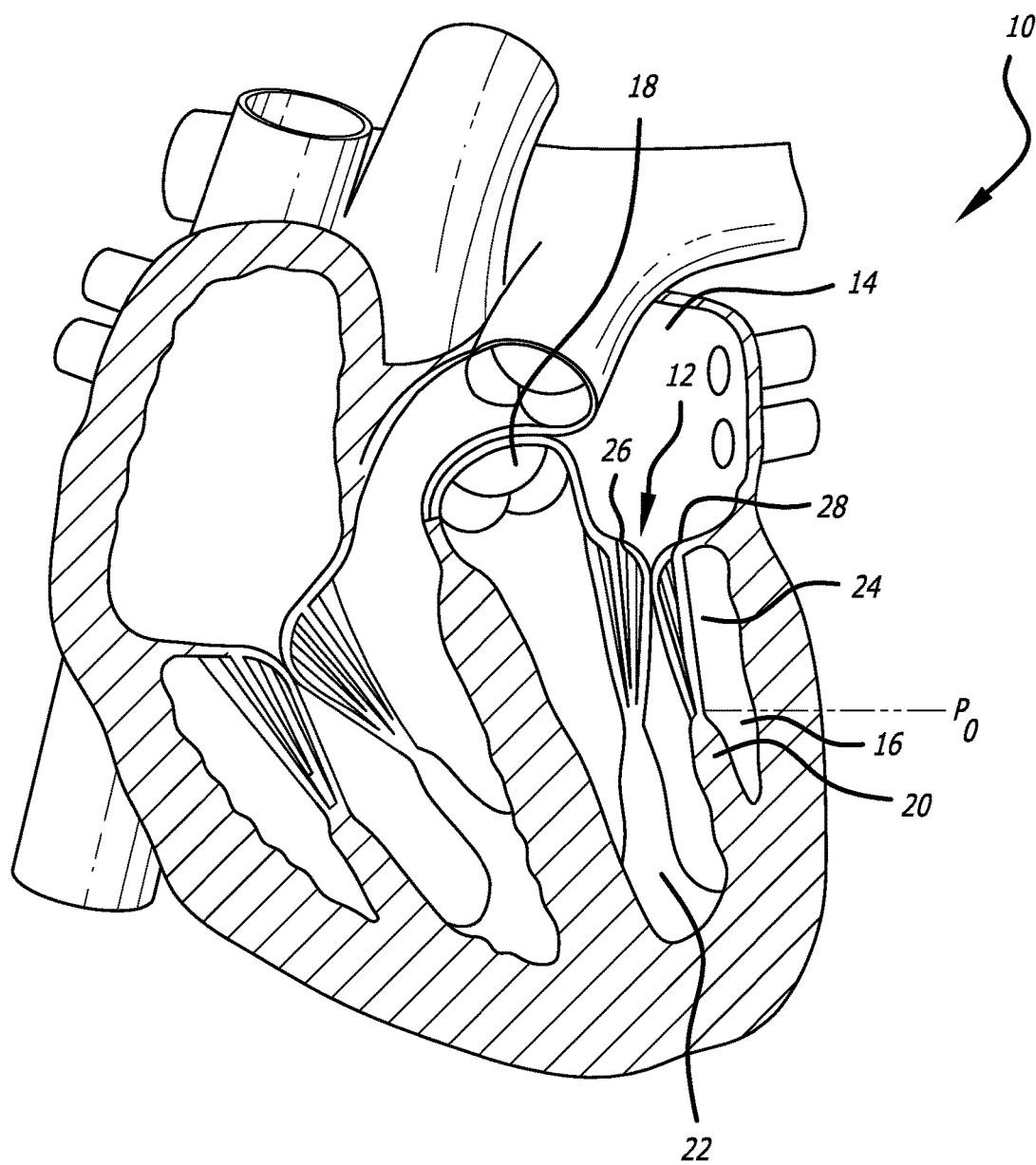
FIG. 1 shows a sectional view of the heart 10 of a human subject.
Figure 2:
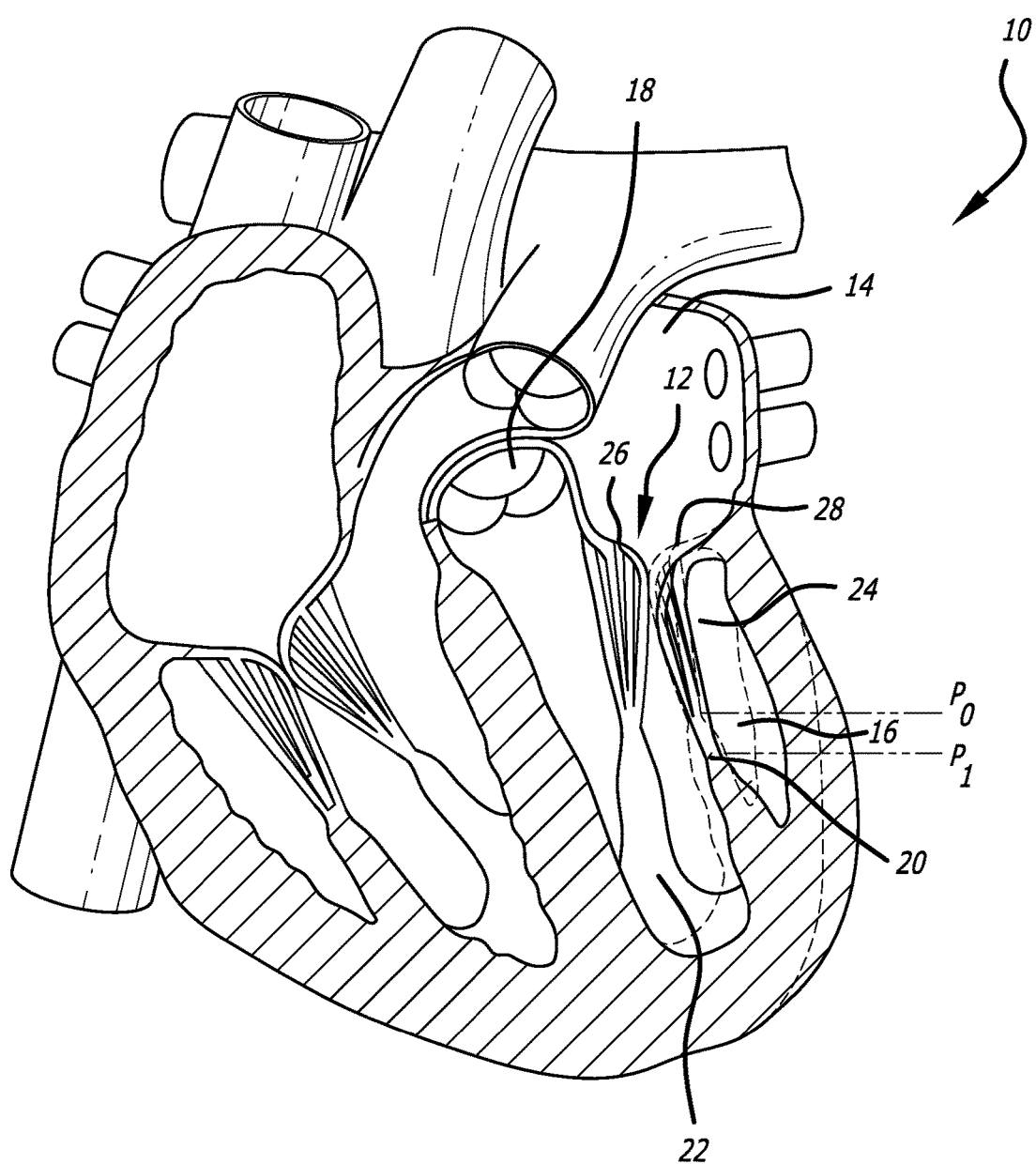
FIG. 2 shows the sectional view of FIG. 1, in which a wall of the heart has fallen due to an ischemic event. Dotted lines indicate where the wall was before it fell.

In one embodiment of the present invention, the tissue penetrating catheter may be used in the following manner to give rise to the beneficial results of the invention, which is to elevate the point of connection between the chordae tendineae 24 and the papillary muscle 20 relative to the balance of the heart structure 10. As shown in FIG. 3, the elevation of this point after an ischemic distortion event in the wall of the heart (such as described above in relation to FIG. 2) and before the present inventive procedure is carried out is at the level marked P1. This level is below the level P0, shown in FIG. 1, which is the level it would be at if the heart were in its previous healthy condition, as explained above with reference to FIG. 1. As a result of the reduced point of attachment at P1, the chordae tendineae have pulled down on the leaflet 28, thereby preventing that leaflet from properly coapting with the opposing leaflet 26, as shown in FIGS. 2 and 3. This results in blood flow backwards through the mitral valve during systole, as indicated by the arrows marked F.

Routes of Access to the Papillary Muscle

As understood with reference to FIG. 3, the catheter may be given access to an external wall surface 30 of the heart at a location opposite one of the papillary muscles and, in the case of FIG. 3, it is the antero-lateral papillary muscle 20, but the invention applies with equal effect to the postero-medial papillary muscle 22. Access to the wall surface 30 may be accomplished in a number of ways. In a first method, the heart may be exposed by "open heart" surgery, to give the operating surgeon direct access to the wall 30. Means of visualization of the interior of the heart itself from outside the heart, where the heart has been exposed as in this method, may include the technique of translumination, under which a very strong light source is introduced into chambers of the heart via fiber optic cable or light source. The brighter the light that is visible from the outside, the thinner the wall—and it may be observed that the darker or thicker papillary muscle may be differentiated. Other methods may include intraoperative transesophageal echocardiography (TEE) and fluoroscopy.

Under such open heart surgery, a first method of approach may be used that is exemplified with reference to FIG. 3. A balloon catheter 100 having a sharp tip 102 may be inserted directly into the wall of the heart and then directly into the location of the papillary muscle 20.

Figure 7:
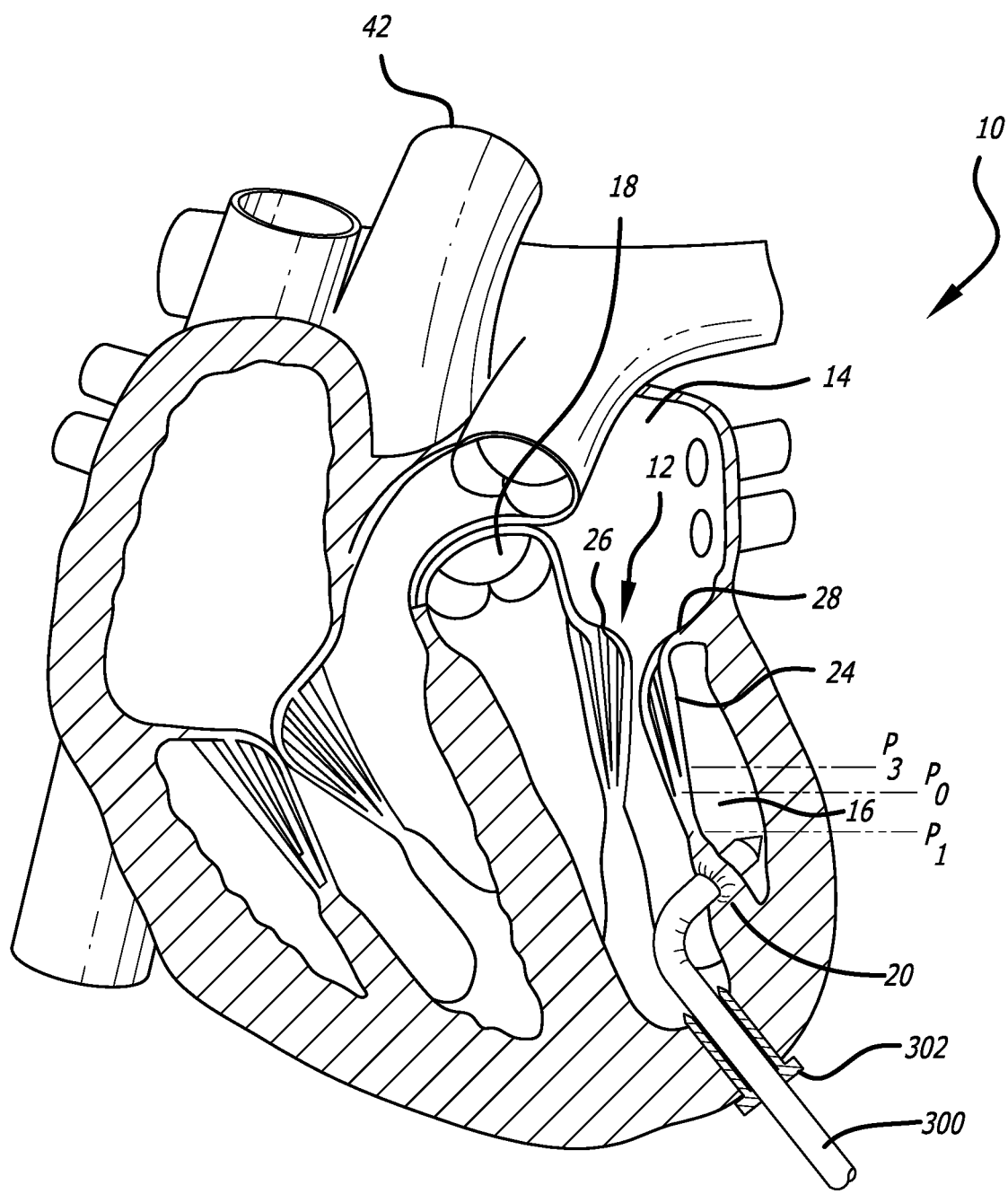
FIG. 7 shows the heart shown in FIG. 2, with a balloon cannula being inserted into a portion of the heart in yet a further alternative embodiment of the invention.

Under a second method of approach, exemplified in FIG. 7, a cannula port 302 may be inserted in the wall 30 of the heart into a location that is adjacent the papillary muscle (that is to say, transapically). A catheter 300 may then be inserted through the cannula 302 and into the space defined by the left ventricle 16. From there, the catheter may be steered using known means for steerable catheters, so that its sharp tip penetrates the papillary muscle laterally and the balloon is advanced until it is lodged securely within the papillary muscle. An advantage of this method is that the papillary muscle is not injured to the same extent as in the embodiment shown in FIG. 3. However, the opening in the wall of the heart into the left ventricle by the cannula port 302 may also create injury complications.

In a further general method of approach, the sharp tip 102 of the tissue penetrating catheter 100 may simply be inserted between the ribs of the patient from the exterior of the patient, and the catheter may be forced towards the heart to reach the desired location. Under the latter method, known means of visualization such as intraoperative transesophageal echocardiography (TEE) and fluoroscopy may be used to monitor the progress of the catheter 100 through the body of the patient, and known means may be used to steer the catheter towards the desired location.

One of ordinary skill in the art will appreciate that while open heart surgery gives the operating surgeon the advantage of much greater accuracy as to the point of penetration into the heart, yet at the same time it has the disadvantage of a more invasive procedure for the patient compared with the alternative method in which insertion is through the ribs from a point exterior the patient. In the case where the patient's chest is opened, typically via a sternotomy, the patient is placed on cardiopulmonary bypass. The need to both open the chest and place the patient on bypass is traumatic and has associated high mortality and morbidity. In a third method, the catheter may be introduced inside the heart to have access to the papillary muscle by transcatheter procedure, as will be described more fully below with reference to FIG. 6.

Thus, having gained access to the exterior of the heart using one of a number of alternative methods, the surgeon pushes the tissue penetrating catheter 100 through the wall 30 and deep into the tissue of the wall and thereafter into the tissue of the antero-lateral papillary muscle 20. Known methods of visualization may be used to locate the tissue penetrating catheter and the attached balloon 104 as it is advanced into the papillary muscle. Care must be used to position the catheter centrally within the tissue making up the muscle, as shown in FIG. 3. At this stage before inflation, the balloon has a maximum outside diameter "D1," as marked in FIG. 3. Once the catheter is centrally positioned, and the balloon 104 is positioned at a desired position vertically through the muscle, the balloon is slowly inflated. The inflation has the effect of separating sheets of tissue comprising the muscle, and stretching the tissue surrounding the balloon, as shown in FIG. 4. At this stage after inflation, the balloon has a maximum diameter of "D2" as marked in FIG. 4.

Inflation.

It will be understood that the speed of inflating the balloon is a feature of the method that should be sensitively implemented. If the inflation is too rapid, the effect may be to damage or tear the muscle tissue. However, it will be appreciated that under some conditions, such as open heart placement of the catheter, the surgeon cannot inflate the balloon too slowly because the patient may be in a precarious temporary position that must be brought to an end with rapidity. Accordingly, the speed of inflation must be sufficiently slow as to allow the muscle fibers that surround the balloon to be gently stretched and elongated, without damaging the performance of the altered muscle. When the balloon 104 is in its inflated condition as shown in FIG. 4, the point of connection between the chordae tendineae may be temporarily lowered in relation to the rest of the heart to a level P2, which may be lower than the level P1—the latter being the point of connection occupied before the balloon inflation began. In this condition, the leaflets may not coapt successfully to form a seal during systole.

Then, when the stretching process has been completed to satisfaction, the balloon 104 is deflated once again, and resumes a configuration substantially similar to that shown in FIG. 3, where the balloon has returned to a diameter substantially equal to D1. By the term "substantially" it is intended to convey the notion that the dimensions are sufficiently similar to allow the catheter to be safely withdrawn from its location within the tissue.

At this stage, then, the catheter may be withdrawn. The end result of this process may be understood with reference to FIG. 5. Here, it is shown that the fibers of the papillary muscle, having been stretched and allowed to extend in an upward direction, now surround a slender opening 32 which was previously occupied by the balloon and which is now a slender cut in the muscle fiber. The stretching results in an effectively elongated papillary muscle 20 with the result that the point of connection between the chordae tendineae is now elevated to a level marked as P3 in FIG. 5. If the muscle stretching has been correctly assessed and achieved, the level P3 will be the same as or close to the level P0 (as described above as being the level it would be in a healthy heart), so that the posterior leaflet 28 will be able to return to a level capable of achieving a satisfactory coaptation with the opposing anterior leaflet 26—as is shown in FIG. 5, with blood regurgitating flow through the mitral valve being blocked by coapting leaflets 26, 28 as indicated by arrows R in FIG. 5.

Pause During Stretching.

However, as an additional step after the balloon is deflated, the catheter may be held in position after the balloon is deflated rather than being immediately withdrawn, and observations and measurements may be taken prior to the removal of the balloon. It will be appreciated that the balloon occupies a large proportion of the total volume of the catheter when the balloon is inflated. Therefore, leaving the catheter in position while the balloon is deflated will not significantly affect the reading. The surgeon may use known methods for assessing whether coaptation has been improved by the procedure thus far. Transesophageal echocardiography and color Doppler are known diagnostic measures of degrees of mitral regurgitation. This can be accomplished in real time, and allows for adjustment of the papillary muscle length by means of the described inflation. If the surgeon concludes that coaptation has not improved adequately, in that the point of attachment between chordae tendineae and muscle has not been elevated sufficiently, she may re-inflate the balloon, and continue to expand it beyond the degree to which it was previously expanded, in an attempt to improve the outcome. This action gives the surgeon some measure of control over the outcome by being able to adjust the final degree to which the point of attachment between chordae tendineae and muscle is lifted.

Application of Anti-Scar Forming Agent

Before the procedure is terminated by withdrawing the balloon, however, the space formed by the balloon may be infused with an agent to prevent the lesion created by the balloon from attempting to heal and form scar tissue, which may have the undesired effect of once again shortening the length of the papillary muscle. In order to achieve the desired result, the inflation balloon may be withdrawn, and may be replaced over a preplaced guidewire by a second balloon configured to define micro-pores that penetrate through the wall of the second balloon. Then, the second balloon may be inflated with an agent suitable for preventing the formation of scar tissue in the space formed by the first balloon. The agent bleeds through the wall of the balloon into the space, and coats the inner tissue lining of the space. The agent may include compounds such as NEOSPORIN®. Further, methods such as cryotherapy may also be used.

Figure 6:
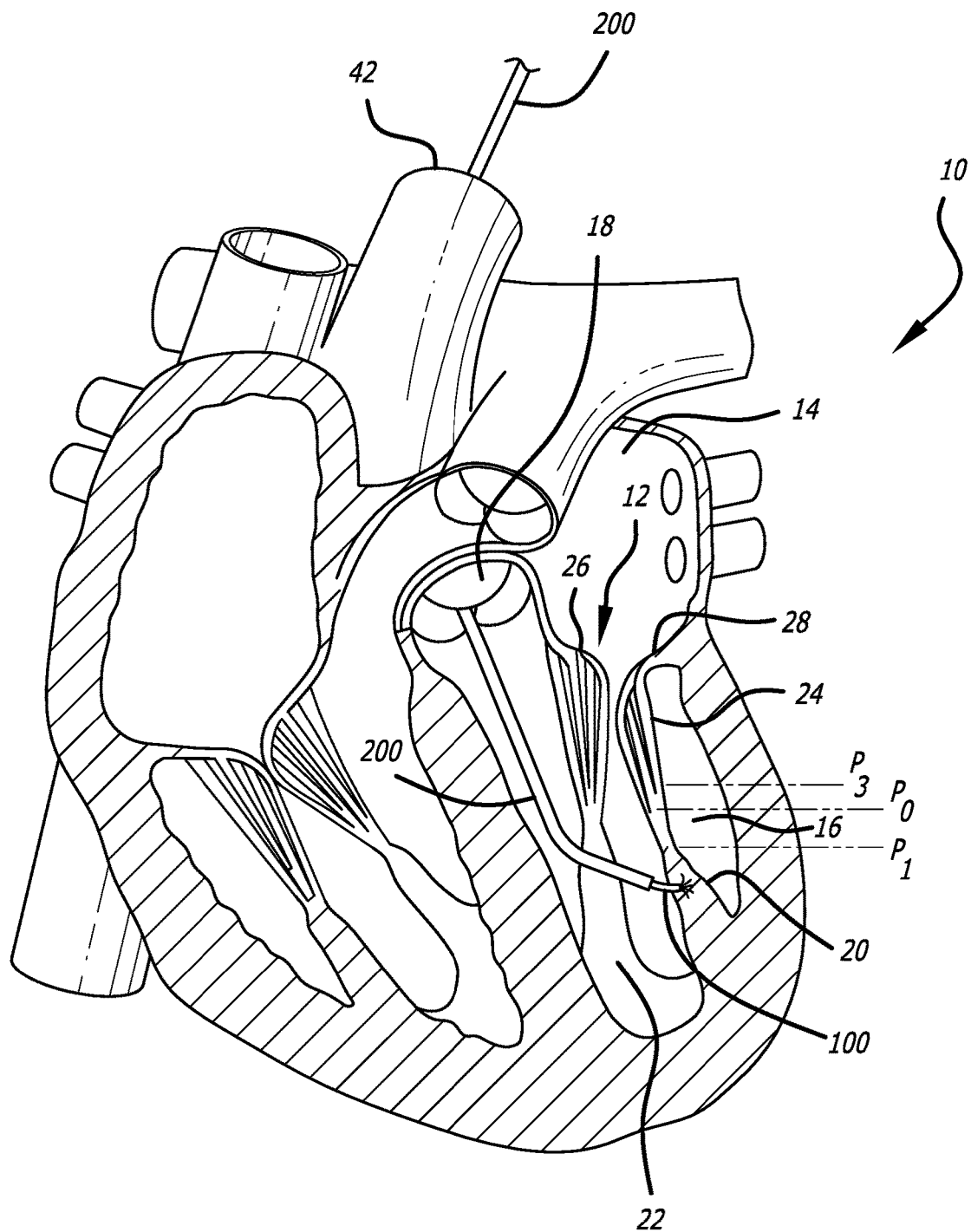
FIG. 6 shows the heart shown in FIG. 2, with a balloon cannula being inserted into a portion of the heart in an alternative embodiment of the invention.

In another embodiment of the invention, the same concept as reflected in FIGS. 3-5 of inserting an inflatable balloon into the papillary muscle may be used, but in in the case of this embodiment a different point of approach by the tissue penetrating catheter may be applied. With reference to FIG. 6, it is shown how a trans-endocardial method for treatment of mitral insufficiency may be conducted in accordance with the present invention. As shown in FIG. 6, in this example, the leaflets 26, 28 of the mitral valve are not in coaptation and an opening 40 exists between the mitral valve leaflets during the systolic phase of the cardiac cycle. To improve coaptation of the mitral valve leaflets, a catheter 200, such as a steerable or non-steerable guide catheter is inserted into as the arterial vasculature and is advanced in retrograde fashion through the aorta 42, through the aortic valve 18 and into the left ventricle 16. The distal end of the catheter 200 is positioned such that it is directed at the antero-lateral papillary muscle 20. Techniques known in the art of medical imaging and/or interventional cardiology and radiology may be used to facilitate positioning of the catheter 200. For example, fluoroscopy (traditional bi-plane or O-arm) as well as ultrasound (2D, 3D or 4D) can be used to position catheter 200. Also, other ventricular mapping systems like three dimensional computed tomography (CT) mapping (e.g., using the CARTO™ mapping systems available from Biosense-Webster, Inc., Diamond Bar, Calif.), other CT scans or MRI scans can be used to map the ventricle to facilitate the desired positioning of the catheter 200. Thereafter, a tissue penetrating catheter 100 such as that described above, may be advanced out of the distal end of the guide catheter 200 and into the myocardium of the antero-lateral papillary muscle 20.

Once again, as with the former embodiment, after the balloon 104 portion of the catheter has been inserted into the muscle, the balloon may be inflated at an appropriate rate to stretch the tissues. As before, visualization may be carried out using known techniques, and the rate of regurgitation may be measured using known techniques. Transesophageal echocardiography and color Doppler are known diagnostic measures of degrees of mitral regurgitation. This can be accomplished in real time, and allows for adjustment of the papillary muscle length by means of the described inflation. After the tissues have been allowed to stretch, the balloon may be deflated, and the rate of regurgitation may be measured. If it is assessed that the rate of regurgitation is still unacceptably high, then the balloon may be inflated again and the muscle tissue stretched still further. This cycle may be repeated more than once.

Thus, by the method of this invention, problems in the prior art may be addressed. For example, considering the prior art that teaches implantation of devices and fillers within the papillary muscle with the purpose of "bulking up" the papillary muscle—that approach suffers the disadvantage that, while the filler may stretch the fiber of the muscle, leaving the filler inside the muscle does not permit the point of connection between the chordae tendineae to move upwardly to an adequate extent, but may in fact cause the point of attachment to move further downwards than it was before the implantation.

Accordingly, there is described a novel system and method that addresses needs in the art. The present invention may, of course, be carried out in other specific ways than those herein set forth without departing from the essential characteristics of the invention. The present embodiments are, therefore, to be considered in all respects as illustrative and not restrictive, while the scope of the invention is set forth in the claims that follow.

We claim:

1. A method for improving function of a cardiac valve in a heart of a patient, the cardiac valve having at least one leaflet that is attached to a papillary muscle, the method comprising the steps of:

inserting an expandable device, that is in a first unexpanded condition and having a first diameter, within tissue that is part of the papillary muscle and thereby, separating tissue that was previously connected together, by a first distance;

expanding the expandable device to a second expanded condition having a second diameter greater than the first diameter, thereby permanently stretching tissue in the papillary muscle and separating the tissue that is part of the papillary muscle by a second distance greater than the first distance;

unexpanding the expandable device to the first unexpanded condition, and thereby returning the tissue that is part of a papillary muscle to a separation of a third distance substantially equal to the first distance; and then removing the expandable device from the patient, without leaving any substance within the tissue that is part of the papillary muscle.

2. The method of claim 1, wherein inserting an expandable device includes inserting a balloon, and expanding the expandable device includes inflating the balloon.

3. The method of claim 1, wherein expanding the expandable device to a second expanded condition includes expanding the expandable device to the second diameter, and then leaving the expandable device for a period of time in the second expanded condition before unexpanding the expandable device.

4. The method of claim 1, wherein inserting an expandable device within tissue that is part of the papillary muscle includes inserting the expandable device from outside the heart, through a wall of the heart, and into the tissue.

5. The method of claim 4, wherein inserting an expandable device includes inserting the expandable device through the wall of the heart into a space defined by the left ventricle, and then into the papillary muscle.

6. The method of claim 1, wherein inserting an expandable device within tissue that is part of the papillary muscle includes inserting the expandable device via an aortic valve and then via a left ventricle before inserting the expandable device within the tissue.

7. The method of claim 1, further including re-expanding the expandable device after the unexpanding step, and before the removing step.

8. The method of claim 7, wherein re-expanding the expandable device includes taking measurements of a degree of coaptation being achieved by leaflets in the heart before the re-expanding step.

9. The method of claim 1, further including treating a surface of tissue that was previously connected to adjacent tissue with a scar inhibiting agent.

10. The method of claim 9, wherein treating a surface with a scar inhibiting agent includes treating the surface with Neosporin.

11. A method for improving function of a cardiac valve in a heart of a patient, the cardiac valve having at least one leaflet that is attached to a papillary muscle, the method comprising the steps of:

inserting an expandable device within tissue that is part of the papillary muscle;

expanding the expandable device and thereby permanently stretching tissue in the papillary muscle;

unexpanding the expandable device and thereby leaving within the tissue a void not previously present within the tissue; and removing the expandable device from the patient without leaving any implant device in the papillary muscle.

12. The method of claim 11, wherein expanding the expandable device includes inflating a balloon.

13. The method of claim 11, after the expanding step, the expandable device is left expanded for a period of time before the unexpanding step.

14. The method of claim 11, wherein inserting an expandable device within tissue that is part of the papillary muscle includes inserting the expandable device from outside the heart, through a wall of the heart, and into the tissue.

15. The method of claim 14, wherein inserting an expandable device includes inserting the expandable device through the wall of the heart into a space defined by the left ventricle, and then into the papillary muscle.

16. The method of claim 11, wherein inserting an expandable device within tissue that is part of the papillary muscle includes inserting the expandable device via an aortic valve and then via a left ventricle before inserting the expandable device within the tissue.

17. The method of claim 11, further including re-expanding the expandable device after the unexpanding step, and before the removing step.

18. The method of claim 17, wherein re-expanding the expandable device includes taking measurements of a degree of coaptation being achieved by leaflets in the heart before the re-expanding step.

19. The method of claim 11, further including treating a surface of tissue that was previously connected to adjacent tissue with a scar inhibiting agent.

20. The method of claim 19, wherein treating a surface with a scar inhibiting agent includes treating the surface with Neosporin.

* * * * *